United States Patent [19]

Ricca

[11] Patent Number: 5,869,712
[45] Date of Patent: Feb. 9, 1999

[54] α-AMINO-SUBSTITUTED ACETIC ACIDS OR ACID SALTS AND THEIR USE IN COSMETICS

[75] Inventor: Jean-Marc Ricca, Lyon, France

[73] Assignee: Rhone-Poulenc Chimie, Courbevoie Cedex, France

[21] Appl. No.: 454,311

[22] PCT Filed: Dec. 10, 1993

[86] PCT No.: PCT/FR93/01223

§ 371 Date: Jun. 19, 1995

§ 102(e) Date: Jun. 19, 1995

[87] PCT Pub. No.: WO94/13621

PCT Pub. Date: Jun. 23, 1994

[30] Foreign Application Priority Data

Dec. 17, 1992 [FR] France .................................. 92 15218

[51] Int. Cl.$^6$ .................................................. C07C 231/00
[52] U.S. Cl. ................................ 554/68; 554/54; 554/59; 564/123; 564/193; 564/215; 564/488
[58] Field of Search .................................. 554/59, 54, 68; 564/123, 193, 215, 488

[56] References Cited

FOREIGN PATENT DOCUMENTS 55-000336  1/1980  Japan .

OTHER PUBLICATIONS

Chemical Abstr. of JP–05'311193, including anticipted compounds, Nov. 1993.

*Primary Examiner*—Gary Geist
*Assistant Examiner*—Deborah D. Carr
*Attorney, Agent, or Firm*—Burns, Doane, Swecker & Mathis, L.L.P.

[57] ABSTRACT

α-Amino-substituted acetic acids or acid salts of formula

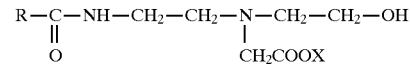

where R represents a hydrogen atom or an alkyl or alkoxy group X represents a hydrogen atom, an alkali metal or alkaline-earth metal or an ammonium residue characterized in that they are totally free of haloacetic acid and alkali metal halide. They are capable of being obtained by reaction, under hot conditions, of glyoxal, or of a precursor of glyoxal, with a secondary amine or one of its salts of formula

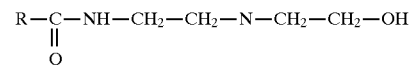

where R represents a hydrogen atom or an alkyl or alkoxy group, optionally followed by hydrolysis. They may be used as amphoteric surface-active agents for the manufacture of cosmetic compositions.

23 Claims, No Drawings

α-AMINO-SUBSTITUTED ACETIC ACIDS OR ACID SALTS AND THEIR USE IN COSMETICS

The subject of the present invention is α-amino-substituted acetic acids or acid salts which are totally free of haloacetic acid and alkali metal halide, as well as a process for the preparation of the said acids or salts and the use of the said α-amino substituted acetic acids or acid salts of very high purity as surface-active agents in cosmetic compositions.

SUMMARY OF THE INVENTION

According to the invention, they are α-amino-substituted acetic acids or acid salts of formula (I)

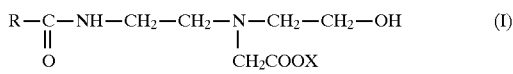

in which formula
R represents a hydrogen atom or a linear or branched and optionally substituted $C_1$–$C_{18}$ alkyl or alkoxy group,
X represents a hydrogen atom, an alkali metal or alkaline-earth metal or an ammonium residue characterized in that they are totally free of haloacetic acid and alkali metal halide.

DESCRIPTION OF THE PREFERRED EMBODIMENTS

The present invention is very particularly aimed at the acid form of N-lauroyl-N'-(2-hydroxyethyl)-N'-(carboxymethyl)ethylenediamine and its salts.

Numerous compounds of general formula (I) and more particularly their inorganic salts are widely employed in the detergent and cosmetics industries as amphoteric agents. Apart from their surfactant qualities, these compounds also show themselves to have, owing to their chemical structure, a very desirable biodegradable nature. By way of a particularly advantageous compound, there may especially be mentioned the sodium salt of N-lauroyl-N'-(2-hydroxyethyl)-N' (carboxymethyl)ethylene-diamine.

These compounds are conventionally prepared from a compound of general formula (II)

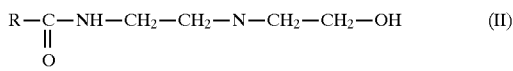

which undergoes condensation with chloracetic acid or with one of its salts.

This synthesis route is, however, not satisfactory for various reasons.

Direct condensation of a chloracetic acid only leads to a poor yield, of the order of 33%, and in addition requires a purification step.

As regards more particularly the inorganic salts of chloracetic acid, they do indeed lead to better yields, but also to the formation of large amounts of impurities such as, for example, sodium chloride in the particular case of sodium chloroacetate. It is then necessary to use awkward purification techniques, of the electrodialysis or osmosis type which, apart from their cost, have the disadvantage of being difficult to implement industrially.

Finally, like its salts, chloracetic acid has an irritant nature which has now been well established.

For these reasons, it is desirable now to have available compounds of formula (I) which are totally free of haloacetic acid and alkali metal halide. In addition, the acids or acid salts of the invention preferably do not contain more than 0.5% of their weight of glycolic acid.

The compounds forming the subject of the invention are capable of being obtained by reaction, under hot conditions, of glyoxal, or of a precursor of glyoxal, with a secondary amine or one of its salts of general formula (II),

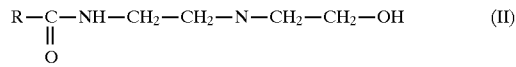

in which R represents a hydrogen atom or a linear or branched and optionally substituted $C_1$–$C_{18}$ alkyl or alkoxy group, optionally followed by hydrolysis.

Apart from the fact that such a process precludes the use of chloroacetic acid or one of its derivatives, it advantageously permits a direct access to the acid form and thus rids itself of the standard inorganic contaminants such as sodium chloride.

The secondary amine of general formula (II) may preferably be obtained by in situ or extemporaneous basic hydrolysis, in the reaction medium, of an imidazoline of general formula (III)

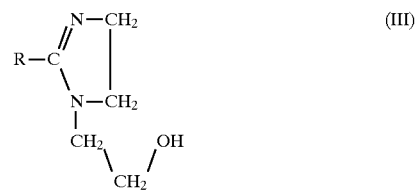

in which formula R represents a hydrogen atom or a linear or branched and optionally substituted $C_1$–$C_{18}$ alkyl or alkoxy group.

Hydrolysis of the imidazoline of general formula (III) is effected in a conventional manner in aqueous medium and in the presence of a base. The base is more particularly sodium hydroxide. A person skilled in the art is able, owing to his technical competences, to reproduce this hydrolysis.

From the point of view of the operating conditions, this process for the preparation of the compounds of formula (I) is relatively easy to implement.

Although the presence of an excess of glyoxal does not affect the progress of the reaction this compound is preferably used in an equimolar amount relative to the secondary amine. In this way the process rids itself of any subsequent purification step.

Precursor of glyoxal is understood to denote any compound which is capable of generating glyoxal in the reaction medium. 4,4',5,5'-tetrahydroxybis[2,2-(1,3-dioxolane)] corresponds in particular to this definition.

The glyoxal used according to the invention preferably takes the form of aqueous solutions containing 30 to 55% by weight of glyoxal. Of course, other soluble forms of glyoxal prove possible for use according to the invention.

These various forms are familiar to a person skilled in the art and will therefore not be redescribed here.

By way of organic solvent capable of being employed according to the invention there may in particular be mentioned water, alcohols such as, for example, ethanol, methanol and the propanols, as well as their mixtures. The solvent is more particularly water.

Reaction under hot conditions is understood to denote, according to the invention, a reaction carried out at a temperature greater than or equal to 60° C.

This is advantageously a temperature between 60° C. and 100° C., and preferably of the order of 80° C.

The reaction time depends on the temperature. As a guide, a reaction carried out at 80° C. is finished in approximately 2 to 3 hours.

This process is particularly useful for preparing the acid form of N-lauroyl-N'-(2-hydroxyethyl)-N'-(carboxymethyl) ethylenediamine. This compound may, for example, be obtained by the condensation reaction, under hot conditions, of glyoxal with N-(2-hydroxyethyl)laurylimidazoline or of 4,4',5,5'-tetrahydroxybis[2,2'-(1,3-dioxolane)] with N-lauroyl-N'-(2-hydroxyethyl)ethylenediamine.

The acid form of the compounds of general formula (I) may be subsequently converted to its salts with alkali metals, alkaline-earth metals or ammonium, by standard neutralization procedures which are familiar to a person skilled in the art and which will therefore not be redescribed here.

By way of neutralization agent which is capable of being employed, there may more specifically be mentioned alkali metal or alkaline-earth metal hydroxides and amines such as aqueous ammonia and triethanolamine.

The compounds of high purity forming the subject of the invention may be used as amphoteric surface-active agents for the manufacture of cosmetic compositions such as shampoos, cleansing milks, etc.

The examples which follow are presented as a guide and cannot be considered as a limit of the scope and spirit of the invention.

EXAMPLE 1

A mixture of N-(2-hydroxyethyl)laurylimidazoline (5 g, 18.7 mmol), water (4.4 g), sodium hydroxide pellets (40 mg) and glyoxal at a concentration of 40% in water (2.7 g, 18.7 mmol) is heated for 8 hours at 80° C. At the end of 8 hours, an assay by capillary electrophoresis indicates a yield of 76% of N-lauroyl-N'-(2-hydroxyethyl)-N'-(carboxymethyl) ethylenediamine.

EXAMPLE 2

A solution of N-(2-hydroxyethyl)laurylimidazoline (5 g, 18.7 mmol) and sodium hydroxide pellets (40 mg) in water (1.06 g) is heated at 80° C. for 1 hour. A mixture of glyoxal at a concentration of 40% in water (2.7 g, 18.7 mmol) and 1-propanol (5 g) is then added and the residual solution is heated for 6 hours at 80° C. An assay by capillary electrophoresis indicates a yield of 85% of N-lauroyl-N'-(2-hydroxyethyl)-N'-(carboxymethyl)ethylene-diamine.

Example 3

A mixture of N-(2-hydroxyethyl)lauryl-imidazoline (10 g, 37.3 mmol), water (2 g) and sodium hydroxide pellets (80 mg) is heated for 1 hour at 80° C. Glyoxal bis(sodium hydrogen sulphite)monohydrate (10.6 g, 37.3 mmol) is then added and the mixture is heated for 6 hours at 80° C. An assay by capillary electrophoresis indicates a yield of 75% of N-lauroyl-N'-(2-hydroxy-ethyl)-N'-(carboxymethyl) ethylenediamine.

EXAMPLE 4

A mixture of N-lauroyl-N'-(2-hydroxyethyl) ethylenediamine (2.5 g, 8.74 mmol), crystallized 4,4',5,5'-tetrahydroxybis[2,2-(1,3-dioxolane)] (0.612 g, 2.9 mmol) and water (9.5 g) is heated for 6 hours at 80° C. An assay by capillary electrophoresis indicates a yield of 97% of N-lauroyl-N'-(2-hydroxyethyl)-N'-(carboxymethyl) ethylenediamine.

EXAMPLE 5

A mixture of N-lauroyl-N'-(2-hydroxyethyl)-ethylenediamine (7.28 g, 25.4 mmol), crystallized 4,4',5,5'-tetrahydroxybis[2,2-(1,3-dioxolane)] (1.783 g, 8.5 mmol) and 1-propanol (10 g) is heated for 12 hours at 80° C.

An assay by capillary electrophoresis indicates a yield of 19% of N-lauroyl-N'-(2-hydroxyethyl)-N'-(carboxymethyl) ethylenediamine.

EXAMPLE 6

A mixture of N-(2-hydroxyethyl)laurylimidazoline (20 g, 74.6 mmol), sodium hydroxide pellets (153 mg,) and water (4.169 g) is heated for 1 hour at 80° C. Water (41.4 g) is then added and a solution of glyoxal at a concentration of 21% in water (21 g) is run in in the course of two hours at 80° C. The reaction mixture is then heated for 6 hours at 80° C. An assay by capillary electrophoresis indicates a yield of 97% of N-lauroyl-N'-(2-hydroxyethyl)-N'-(carboxymethyl) ethylenediamine.

The impurity, foaming power and viscosity-increasing power profile characteristics of the amphoteric surface-active agent prepared in Example 6 are as follows.

| Impurities | | | |
| --- | --- | --- | --- |
| pH (aqueous) solution at a concentration of 10%) | Solids content (% by weight) | NaCl (% by weight) | Glycolate (% by weight) |
| 8.0 | 30 | 0 | 0.5 |

Foaming power

The foaming power was determined according to the modified Ross-Miles test (standard AFNOR T-73 404) at room temperature, at a concentration of 0.1%.

| Volume of foam (in ml) |
| --- |
| 310 |

Viscosity-increasing power

This is measured using the following formulation

| | |
| --- | --- |
| amphoteric surface-active agent prepared (Example 6) | 35% |
| sodium lauryl ether sulphate containing 3 units of ethylene oxide (aqueous solution at a concentration of 28%) | |
| distilled water | 57% |

The NaCl concentration varies from 0 to 5%; addition of NaCl increases the viscosity of the medium.

| Solids content (%) | Viscosity NaCl 0% | (mPa.s.) NaCl 3% | NaCl 5% |
| --- | --- | --- | --- |
| 30 | 2 | 51 | 2,000 |

EXAMPLE 7

Shampoo

N-lauroyl-N'-(2-hydroxyethyl)-N'-(carboxy-methyl) ethylenediamine obtained according to Example 4 is introduced into a shampoo formulation as follows:

| Components | % active substance | % weight |
|---|---|---|
| Sodium lauryl ether sulphate | 28.3 | 36 |
| N-Lauroyl-N'-(2-hydroxyethyl-N'-carboxymethyl)-ethylenediamine | 50 | 4 |
| Cocoamidopropyl betaine | 35 | 4 |
| Polyquaternium-17 | | 0.5 |
| Coconut diethanolamide | | 1.5 |
| Sodium benzoate | | 0.2 |
| Coloring agent | | 0.1 |
| Citric acid | | qs |
| Sodium chloride | | qs |
| Perfume | | qs |
| Distilled water | | qs 100 |

This shampoo formulation has a pH of 6.4 and a viscosity of 1678 mPa.s.

The use of the acid form of N-lauroyl-N'-(2-hydroxyethyl)-N'-(carboxymethyl)ethylenediamine makes it possible to limit considerably the amounts of citric acid required to obtain a pH of 6.4.

EXAMPLE 8

Baby cleansing milk

The compound obtained according to Example 4 is also introduced into a baby cleansing milk formulation. In order to do this, hydroxypropyl guar gum is introduced into water with vigorous stirring, and the pH is then adjusted to 5–6 with citric acid. The guar gum solution is subsequently introduced into the mixture of surfactants and N-lauroyl-N'-(2-hydroxyethyl)-N'-(carboxymethyl)ethylenediamine, and the pH is adjusted to 7 with citric acid.

| Components: | % of active material | % by weight |
|---|---|---|
| N-lauroyl-N'-(2-hydroxyethyl)-N'-(carboxymethyl)ethyl-enediamine | 50.0 | 20.0 |
| Hydroxypropyl guar gum trimonium chloride | | 0.3 |
| Bromonitrodioxane | 10.0 | 0.2 |
| Citric acid | 30.0 | qs |
| Perfume | | 0.2 |
| Coloring agent | 1.0 | 0.1 |
| Distilled water | | qs 100 |

The pH is of the order of 7.5 and the viscosity is 10 mPa.s.

I claim:

1. Process for the preparation of α-amino-substituted acetic acids or acid salts of formula (I)

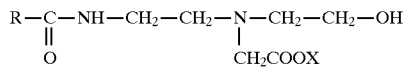
$$\begin{array}{c} \text{R}-\text{C}-\text{NH}-\text{CH}_2-\text{CH}_2-\text{N}-\text{CH}_2-\text{CH}_2-\text{OH} \\ \parallel \quad\quad\quad\quad\quad\quad\quad\quad\quad\quad | \\ \text{O} \quad\quad\quad\quad\quad\quad\quad\quad\quad\quad \text{CH}_2\text{COOX} \end{array}$$

in which formula

R represents a hydrogen atom or a linear or branched and optionally substituted $C_1$–$C_{18}$ alkyl or alkoxy group X represents a hydrogen atom, an alkali metal or alkaline-earth metal or an ammonium residue characterized in that glyoxal or a precursor of glyoxal is reacted by condensation, at a reaction temperature, with a secondary amine or with one of its salts of general formula (II),

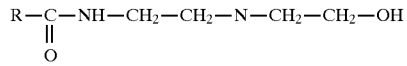
$$\text{R}-\text{C}-\text{NH}-\text{CH}_2-\text{CH}_2-\text{N}-\text{CH}_2-\text{CH}_2-\text{OH}$$
$$\parallel$$
$$\text{O}$$

in which R represents a hydrogen atom or a linear or branched and optionally substituted $C_1$–$C_{18}$ alkyl or alkoxy group, optionally followed by hydrolysis.

2. Process according to claim 1, wherein the amine of general formula (II) is obtained by in situ or extemporaneous basic hydrolysis, in the reaction medium, of an imidazoline of general formula (III)

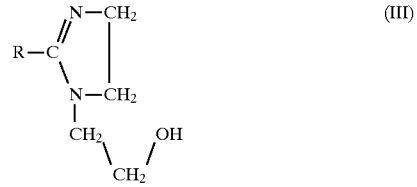

in which R represents a hydrogen atom or a linear or branched and optionally substituted $C_1$–$C_{18}$ alkyl or alkoxy group.

3. Process according to claim 1, wherein the reaction temperature is greater than or equal to 60° C.

4. Process according to claim 1, wherein said reaction temperature is between approximately 60° and 100° C.

5. Process for the preparation of N-lauroyl-N'-(2-hydroxyethyl)-N'-(carboxymethyl)ethylenediamine or its salts with alkali metals, alkaline-earth metals or ammonium, by the condensation reaction, under hot conditions, of glyoxal with N-(2-hydroxyethyl)laurylimidazoline or 4,4',5,5'-tetrahydroxybis[2,2-(1,3-dioxolane)] with N-lauroyl-N'-(2-hydroxyethyl)ethylenediamine.

6. Process according to claim 1, wherein glyoxal or the precursor of glyoxal and the secondary amine are placed together in a molar ratio equal to 1.

7. Process according to claim 5, wherein the reaction is carried out in the presence of water.

8. N-Lauroyl-N'-(2-hydroxyethyl)-N'-(carboxymethyl) ethylenediamine or its salts with alkali metals, alkaline-earth metals or ammonium, which are capable of being obtained by the condensation reaction, at a reaction temperature, of glyoxal with N-(2-hydroxyethyl)laurylimidazoline or 4,4',5,5'-tetrahydroxybis[2,2-(1,3-dioxolane)] with N-lauroyl-N'-(2-hydroxyethyl)ethylenediamine.

9. N-Lauroyl-N'-(2-hydroxyethyl)-N'-(carboxymethyl) ethylenediamine or its salts with alkali metals, alkaline-earth metals or ammonium, according to claim 8, the reactants are brought together in a molar ratio equal to 1.

10. N-Lauroyl-N'-(2-hydroxyethyl)-N'-(carboxymethyl) ethylenediamine or its salts with alkali metals, alkaline-earth metals or ammonium, according to claim 8, wherein the reaction temperature is greater than or equal to 60° C.

11. N-Lauroyl-N'-(2-hydroxyethyl)-N'-(carboxymethyl) ethylenediamine or its salts with alkali metals, alkaline-earth metals or ammonium, according to claim 8, wherein said reaction temperature is between approximately 60° C. and 100° C.

12. N-lauroyl-N'-(2-hydroxyethyl)-N'-(carboxymethyl) ethylenediamine or its salts with alkali metals, alkaline-earth metals or ammonium, according to claim 8, wherein the condensation reaction is carried out in the presence of water.

13. α-Amino-substituted acetic acids or acid salts of formula (I)

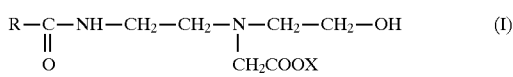

in which formula
  R represents a hydrogen atom or a linear or branched and optionally substituted $C_1$–$C_{18}$ alkyl or alkoxy group,
  X represents a hydrogen atom, an alkali metal or alkaline-earth metal or an ammonium residue which are totally free of haloacetic acid and alkali metal halide.

14. α-Amino-substituted acetic acids or acid salts according to claim 13, which they contain no more than 0.5% of their weight of glycolic acid.

15. A cosmetic composition comprising an amphoteric surface active agent comprising the α-amino-substituted acetic acids or acid salts according to claim 13.

16. N-lauroyl-N'-(2-hydroxyethyl)-N'-(carboxymethyl) ethylenediamine or its salts with alkali metals, alkaline-earth metals or ammonium, which are totally free of haloacetic acid and alkali metal halide.

17. N-lauroyl-N'-(2-hydroxyethyl)-N'-(carboxymethyl) ethylenediamine or its salts with alkali metals, alkaline-earth metals or ammonium, according to claim 3, which contains glycolic acid in an amount between 0% and 0.5% by weight.

18. α-Amino-substituted acetic acids or acid salts of formula (I)

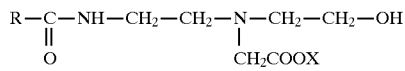

in which formula
  R represents a hydrogen atom or a linear or branched and optionally substituted $C_1$–$C_{18}$ alkyl or alkoxy group,
  X represents a hydrogen atom, an alkali metal or alkaline-earth metal or an ammonium residue, which acids or salts are totally free of haloacetic acid and alkali metal halides and are capable of being obtained by reaction, at a reaction temperature, of glyoxal or of a precursor of glyoxal, with a secondary amine or one of its salts of formula (I),

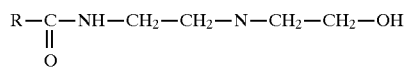

in which R represents a hydrogen atom or a linear or branched and optionally substituted $C_1$–$C_{18}$ alkyl or alkoxy group, optionally followed by hydrolysis.

19. Acids or acid salts according to claim 18, wherein the amine of formula (II) is obtained by in situ or extemporaneous basic hydrolysis, in the reaction medium, of an imidazoline of formula (III)

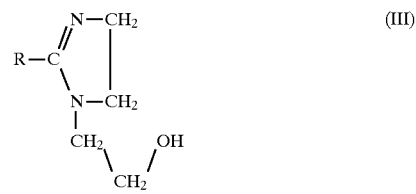

in which R represents a hydrogen atom or a linear or branched and optionally substituted $C_1$–$C_{18}$ alkyl or alkoxy group.

20. Acids or acid salts according to claim 18, wherein glyoxal or the precursor of glyoxal and the secondary amine are brought together in a molar ratio equal to 1.

21. Acids or acid salts according to claim 18, wherein said reaction temperature is greater than or equal to 60° C.

22. Acids or acid salts according to claim 21, wherein the reaction temperature is between approximately 60° and 100° C.

23. Acids or acid salts according to claim 18, wherein the reaction is carried out in the presence of water.

* * * * *